United States Patent
Lam et al.

(10) Patent No.: US 10,039,466 B2
(45) Date of Patent: Aug. 7, 2018

(54) APPARATUS FOR DETECTION OF ELECTRICAL SIGNALS OF A BIOLOGICAL SUBJECT AND ELECTRODE THEREOF, AND METHOD OF MANUFACTURE THEREOF

(71) Applicant: CITY UNIVERSITY OF HONG KONG, Hong Kong (HK)

(72) Inventors: Raymond Hiu-wai Lam, Hong Kong (HK); Tinkei Cheng, Hong Kong (HK); Dinglong Hu, Hong Kong (HK)

(73) Assignee: CITY UNIVERSITY OF HONG KONG, Kowloon Tong (HK)

( * ) Notice: Subject to any disclaimer, the term of this patent is extended or adjusted under 35 U.S.C. 154(b) by 731 days.

(21) Appl. No.: 14/607,110

(22) Filed: Jan. 28, 2015

(65) Prior Publication Data
US 2016/0213269 A1 Jul. 28, 2016

(51) Int. Cl.
A61B 5/04 (2006.01)
A61B 5/0408 (2006.01)
A61B 5/00 (2006.01)

(52) U.S. Cl.
CPC ............ *A61B 5/0408* (2013.01); *A61B 5/683* (2013.01); *A61B 2562/0209* (2013.01); *A61B 2562/125* (2013.01); *A61B 2562/164* (2013.01)

(58) Field of Classification Search
CPC . A61B 5/0408; A61B 5/683; A61B 2562/125; A61B 2562/164; A61B 2562/0209
See application file for complete search history.

(56) References Cited

U.S. PATENT DOCUMENTS

| | | | |
|---|---|---|---|
| 3,599,629 A | 8/1971 | Gordy | |
| 3,845,757 A | 11/1974 | Weyer | |
| 4,370,697 A * | 1/1983 | Haberl | ................ G01L 1/146 361/283.1 |
| 2004/0010303 A1* | 1/2004 | Bolea | ................ A61B 5/02028 607/118 |
| 2014/0088397 A1* | 3/2014 | Chon | ................ A61B 5/0424 600/384 |

OTHER PUBLICATIONS

Richard B. Reilly et al., II.3. Electrograms (ECG, EEG, EMG, EOG), Basic Engineering for Medics and Biologists, IOS Press, 2010.
E. Huigen et al., Investigation into the Origin of the Noise of Surface Electrodes, Med. Biol. Eng. Comput., 2002, 40, pp. 332-338.
A. Searle, A Direct Comparison of Wet, Dry and Insulating Bioelectric Recording Electrodes, Physiol. Meas. 21, 2000, pp. 271-283.

(Continued)

*Primary Examiner* — Lindsey G Wehrheim
(74) *Attorney, Agent, or Firm* — Melvin Li; Heslin Rothenberg Farley & Mesiti PC (57) ABSTRACT

There is provided an apparatus for detection of electrical signals of a biological subject. The apparatus comprises an electrode acting as a conductor for contact with skin of the subject. The electrode includes a first sheet material acting as a base layer and a plurality of pillars members extending from the first sheet material. The apparatus is free of gel or wet gel acting as an electrical conductive media.

19 Claims, 5 Drawing Sheets

(56) References Cited

OTHER PUBLICATIONS

Madison S. Spach, M.D. et al., Skin-Electrode Impedance and Its Effect on Recording Cardiac Potentials, Circulation, vol. XXXIV, Oct. 1966.
Pierre Leleux et al., Ionic Liquid Gel-Assisted Electrodes for Long-Term Cutaneous Recordings, Adv. Healthcare Mater. 2014, 3, pp. 1377-1380.
Chih-Yuan Chen et al., A Low-Power Bio-Potential Acquisition System with Flexible PDMS Dry Electrodes for Portable Ubiquitous Healthcare Applications, Sensors, 2013, 13, 3077-3091.
Chih-Yuan Chen et al., Flexible PDMS Electrode for One-Point Wearable Wireless Bio-Potential Acquisition, Sensors and Actuators A 203, 2013, 20-28.
Giulio Ruffini et al., A Dry Electrophysiology Electrode Using CNT Arrays, http://arXiv.org/abs/physics/0510145 Published online Jul. 17, 2006.
Chia-Lin Chang et al., A Power-Efficient Bio-Potential Acquisition Device with DS-MDE Sensors for Long-Term Healthcare Monitoring Applications, Sensors, 2010, 10, 4777-4793.
N.S. Dias et al., New Dry Electrodes Based on Iridium Oxide (IrO) for Non-Invasive Biopotential Recordings and Stimulation, Sensors and Actuators A 164, 2010, 28-34.
Lun-De Liao et al., Design, Fabrication and Experimental Validation of a Novel Dry-Contact Sensor for Measuring Electroencephalography Signals Without Skin Preparation, Sensors, 2011, 11, 5819-5834.
Rigo Pantoja et al., Silicon Chip-Based Patch-Clamp Electrodes Integrated with PDMS Microfluidics, Biosensors and Bioelectronics 20, 2004, 509-517.
Marc A. Uger et al., Monolithic Microfabricated Valves and Pumps by Multilayer Soft Lithography, Science, vol. 288, Apr. 7, 2000.
George M. Whitesides et al., Soft Lithography in Biology and Biochemistry, Annu. Rev. Biomed. Eng. 2001, 3:335-73.
Tao Deng et al., Prototyping of Masks, Masters, and Stamps/Molds for Soft Lithography Using an Office Printer and Photographic Reduction, Analytical Chemistry, Jul. 15, 2000, vol. 72, 3176-3180.
Michael J. Owen, The Surface Activity of Silicones: A Short Review, American Chemical Society, 1980.
Xize Niu et al., Characterizing and Patterning of PDMS-Based Conducting Composites, Adv. Mater. 2007, 19, 2682-2686.
Jennifer M. Mann et al., A Silicone-Based Stretchable Micropost Array Membrane for Monitoring Live-Cell Subcellular Cytoskeletal Response, Lab Chip, 2012, 12, 731-740.
Raymond H.W. Lam et al., Elastomeric Microposts Integrated into Microfluidics for Flow-Mediated Endothelial Mechanotransduction Analysis, Lab Chip, 2012, 12, 1865-1873.
Cuiwei Li et al., Detection of ECG Characteristic Points Using Wavelet Transforms, IEEE Transactions of Biomedical Engineering, vol. 42, No. 1, Jan. 1995.
P. Zipp, Recommendations for the Standardization of Lead Positions in Surface Electromyography, Eur J Appl Physiol, 1982, 50:41-54.
Ko Keun Kim et al., Common Mode Noise Cancellation for Electrically Non-Contact ECG Measurement System on a Chair, Proceedings of the 2005 IEEE, Engineering in Medicine and Biology 27th Annual Conference.

* cited by examiner

APPARATUS FOR DETECTION OF ELECTRICAL SIGNALS OF A BIOLOGICAL SUBJECT AND ELECTRODE THEREOF, AND METHOD OF MANUFACTURE THEREOF

FIELD OF THE INVENTION

The present invention is concerned with an apparatus for detection of electrical signals of a biological subject, an electrode for use in such apparatus and/or a method of manufacture such apparatus or such electrode.

BACKGROUND OF THE INVENTION

There are a variety of apparatus for use in detection of conditions of a biological subject. One common example of such apparatus makes use of a gel pad acting as an electrode for detection of electrical signals of the subject. In use, the gel pad is placed on the skin surface of the subject. Such apparatus or gel pad however is disadvantageous in a number of ways. First, the gel pad provides an unpleasant sensation of wetness, coldness or otherwise discomfort which is unacceptable by some users. Some users even develop allergies to the electrode. Further, the gel pad is often difficult to be sanitized, rendering it necessary be disposable after single use of a user. Even when used by the same user, the gel pad often has limited life span, and replacement of the gel pad is needed in only several uses in any event. Yet, further conventional electrodes are found to be somewhat unreliable in achieving good conducting contact with skin surface, or otherwise in transmitting signals accurately or reliably.

The present invention seeks to address the aforementioned problems, or at least to provide an alternative to the public.

SUMMARY OF THE INVENTION

There is provided an apparatus for detection of electrical signals of a biological subject, comprising an electrode acting as a conductor for contact with skin of the subject, the electrode including a first sheet material acting as a base layer and a plurality of pillars members extending from the first sheet material, wherein the apparatus is free of gel or wet gel acting as an electrical conductive media.

Preferably, the apparatus may be an electrocardiographic apparatus.

In an embodiment, the pillars may have a cylindrical configuration. A radius of the pillars, a height of the pillars, a center to center distance between two adjacent pillars may be 150 um to 1 mm, 100 um to 2 mm and 500 um to 5 mm, respectively. The radius of said pillars, the height of the pillars, the center to center distance between the two adjacent pillars may be substantially 200 um, 600 um and 1.5 mm, respectively.

In another embodiment, the electrode may include a second sheet material, wherein the pillars may be situated between the first and second sheet materials. One of the first and second sheet materials may be adapted to contact the skin of the subject, and the other sheet material may be provided with a conducting wire for connection with detection circuitry of the apparatus, and wherein the sheet material adapted to contact the skin may be conformable to a surface or curvature of the skin.

Advantageously, the electrode may be made of polymeric organo-silicon compounds and carbon black. The organo-silicon compounds may be polydimethylsiloxane (PDMS). The carbon black may be in the form of powder suspended or otherwise incorporated in the polymeric organo-silicon compounds. The weight ratio of the carbon black and the organo-silicon compounds may be 1:3 to 1:19, or preferably 1:4 to 1:5.6.

In an embodiment, the electrode may be provided with regions between the pillar units, the regions being made of polymeric organo-silicon compounds but not carbon black. There may be provided a gap to surround the pillar units, and the gap may be surrounded by the regions.

Suitably, the pillar units may be adapted to flex sideway. The pillar units may be substantially longer than the thickness of the first or second sheet material.

According to a second aspect of the present invention, there is provided an electrode for use in an apparatus for detection of electrical signals of a biological subject, comprising members made of polymeric organo-silicon compounds and carbon black, and is free of gel or wet gel acting as an electrical conductive media.

Preferably, the said organo-silicon compounds may be polydimethylsiloxane (PDMS), the carbon black may be in the form of powder suspended or otherwise mixed in said organo-silicon compounds, and the ratio of the carbon black and the organo-silicon compounds is 1:4 to 1:5.6.

In an embodiment, the electrode may comprise a first base member and a second base member and a plurality of cylindrical pillar units positioned between the first and second base members, wherein a radius of said pillars, a height of said pillars, a center to center distance between said two adjacent pillars are 150 um to 1 mm, 100 um to 2 mm and 500 um to 5 mm, respectively.

BRIEF DESCRIPTION OF THE DRAWINGS

Some embodiments of the present invention will be explained below, with reference to the accompanied drawings, in which:—

DETAILED DESCRIPTION OF PREFERRED EMBODIMENTS OF THE INVENTION

The present invention is concerned with an apparatus for detection of electrical signals of a biological subject, an electrode for use in such apparatus and a method of manufacturing such apparatus or such electrode. Specific embodiments are concerned with contact-type of bio-potential electrodes for use in, for example, electrocardiographic (ECG) signal detection. The electrodes serve to maintain a direct physical contact with a biological subject, e.g. skin surface of a human patient but without the use of conductive pastes or gel. In other words, such electrodes are considered as dry electrodes.

The electrodes make use of polymeric organosilicon compounds, although studies leading the present invention demonstrate that polydimethylsiloxane (PDMS) is particular suitable for use as a base material candidate for making the electrodes. Polymeric organosilicon compounds are also known as silicones. In addition to the base material, conductive particles, preferably acetylene black, are added into the base material in order to provide electrical conductivity to the base material. Studies in the form of abundant material tests leading to the present invention demonstrate that the ratio of the acetylene black particles and the base material ranges from 1:3 to 1:19, or preferably 1:4 to 1:5.6. The specific ratio of the conductive particles and the base material can be adjusted in accordance to the specific application of the electrode in use, including varying the ratio in different portions of the same electrode. Such ratio is heavily dependent on the choice of conductive particles and such particles' compactification and aggregate dimensions. For instance, material tests leading to the present invention has identified a ratio of roughly 2:3 to 2:1 for graphite powder and 2:1 to 9:1 for silver nanoparticles. Different ECG or bio-signal detection may require electrode with different conductive particles to base material ratio. Electrodes of the present invention are to be contrasted with conventional gel or wet gel type electrodes.

Figure 1:
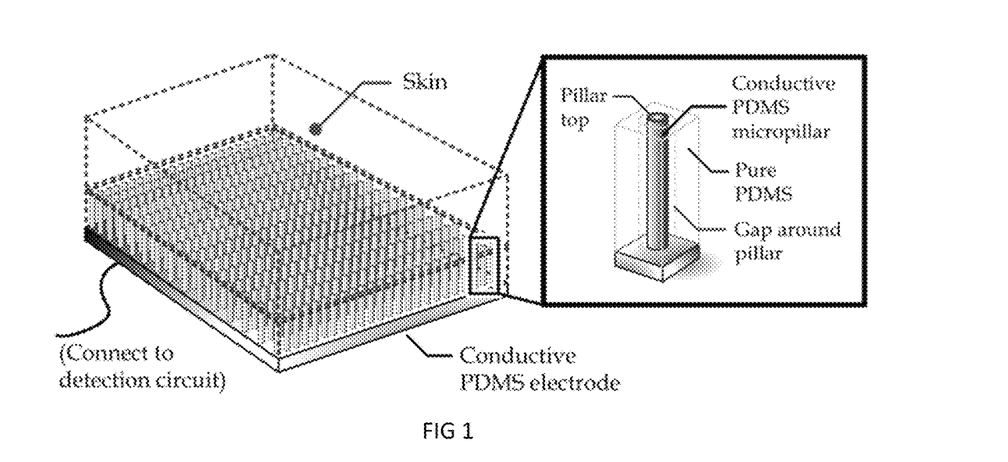
FIG. 1 is a schematic diagram showing an embodiment an electrode for use in an apparatus according to the present invention.

One embodiment of an electrode in accordance with the present invention is illustrated in FIG. 1. FIG. 1 is a schematic diagram showing a portion of the electrode three-dimensionally. Left portion of FIG. 1 shows that the electrode has two main portions, mainly a lower layer or base portion in the form of a sheet material, and an upper layer or relatively stiff portion compared to the base portion. The base portion is made of organosilicon compounds in which carbon powder in the form of acetylene black is suspended. The upper portion includes a plurality of upstanding micropillars extending from the base portion. The micropillars are also made of organosilicon compounds in which acetylene black, a subtype of carbon black, is suspended. The micropillars and the base portion may be integrally formed or bonded via plasma bonding. There may be clearance between and surrounding the micropillars. These regions are incompletely filled with a material made of an organosilicon compound but without carbon black. Despite the presence of the filler made of the organosilicon compounds, there can be a gap surrounding each of the micropillars. Please refer to right portion of FIG. 1 for graphic illustration. It is to be noted that the base portion is for connection to a detection unit of for example an electrocardiographic apparatus. The upper portion is for contacting skin surface of a patient in use. It is also to be noted the upper portion is free from using a gel or wet-gel type material.

The base portion is configured to be sufficiently thin or flexible such that it can conform to skin surface of a user and at the same time absorb shocks or strain sustained in use. On the other hand, the micropillars are relatively rigid compared to the base portion such that minimal interruption to the conductivity would result even when the base portion is under shock, strain or deformation. To be more accurate, the embedded micropillar structure do not deform sensitively to the lateral stretch on the entire flexible electrode, due the high aspect ratios of the micro-structures. In other words, the stretch propagates mainly over the base surfaces. Notably, in the present embodiment's application in ECG sensing, the electrical conduction direction is along the axisymmetry axis of the micro-pillars. Therefore, the representative geometry and hence the electrical properties of the micro-structured flexible ECG electrode can be kept consistent upon stretch. In some embodiments, the pillars may have a height which is substantially longer than the thickness of the base portion. Such configuration allows the conductivity of the pillars to remain stable in use.

The base portion and the micropillars are configured with an improvised conductivity. As explained above, the organosilicon compound (e.g. PDMS) has been added with carbon powder. In one embodiment, the ratio of carbon black and PDMS is 1:5. The use of the aforementioned microstructure as the electrode reduces deformation of the electrical signal conducting micropillars, and ensures conductivity of the electrode at a desired level stably.

Figure 3:
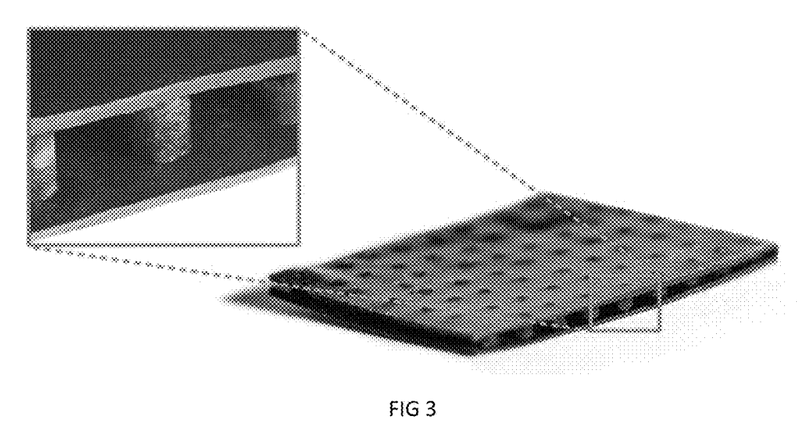
FIG. 3 photographical images of another embodiment of an electrode according to the present invention.

FIG. 3 are photographic images of another embodiment of an electrode made in accordance with the present invention. This electrode is different from the electrode in FIG. 1 in that there is a lower layer and an upper layer sandwiching the pillars. One of the layers is configured to contact a skin surface of a user, and the other layer is connected to an apparatus via an electric wire.

Experiment

Two technical characteristics of an electrode of the present invention are its improved conductivity and its signal stability under deformation. Studies show that that the conductivity is increased by almost two-fold when there is no deformation. Please see FIG. 2A. Even under deformation, the conductivity can remain stable. It is to be noted that under disturbances such as body movements and compression by external objects can cause deformation of flexible electrodes, changes in the electrode conductivity and hence induce signal noise. Experiments were conducted to quantify the relations between the strain increment and conductivity variation of the conductive-PDMS substrates. In the experiments, selected composite of 20% acetylene black in PDMS was used for analysis. Stretches on the conductive-PDMS specimens were induced using a mechanical tester (MTS Alliance RT/30) at a rate of 1 mm/min for a total distance of 1 mm (maximum strain of 5%); and the conductivity along the direction of substrate thickness was measured. Same experiments were performed to obtain characteristics of micro-engineered electrodes under stretch. The experimental results were then compared with the bulk conductive-PDMS substrate under the same testing conditions.

Figure 2A:
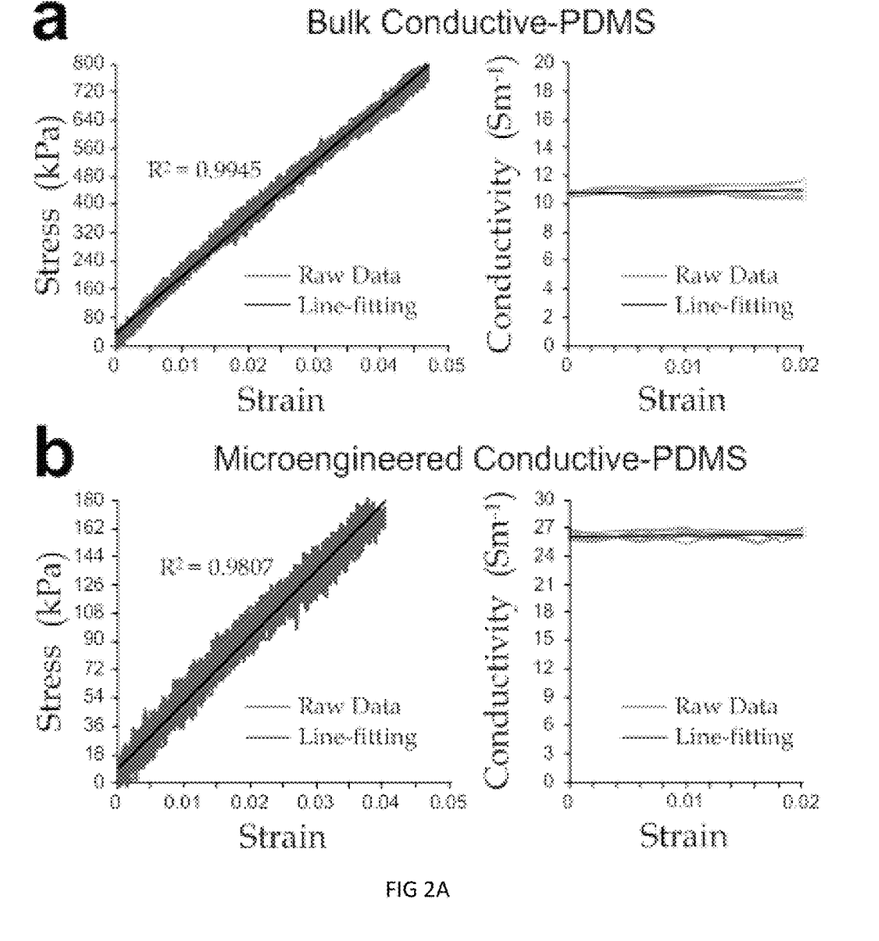
FIG. 2A including graphs showing stress-strain curves and conductivities as functions of tensile strain for (a) bulk conductive-PDMS and (b) micro-engineered conductive-PDMS dry electrode embedded with micropillars.
Figure 2B:
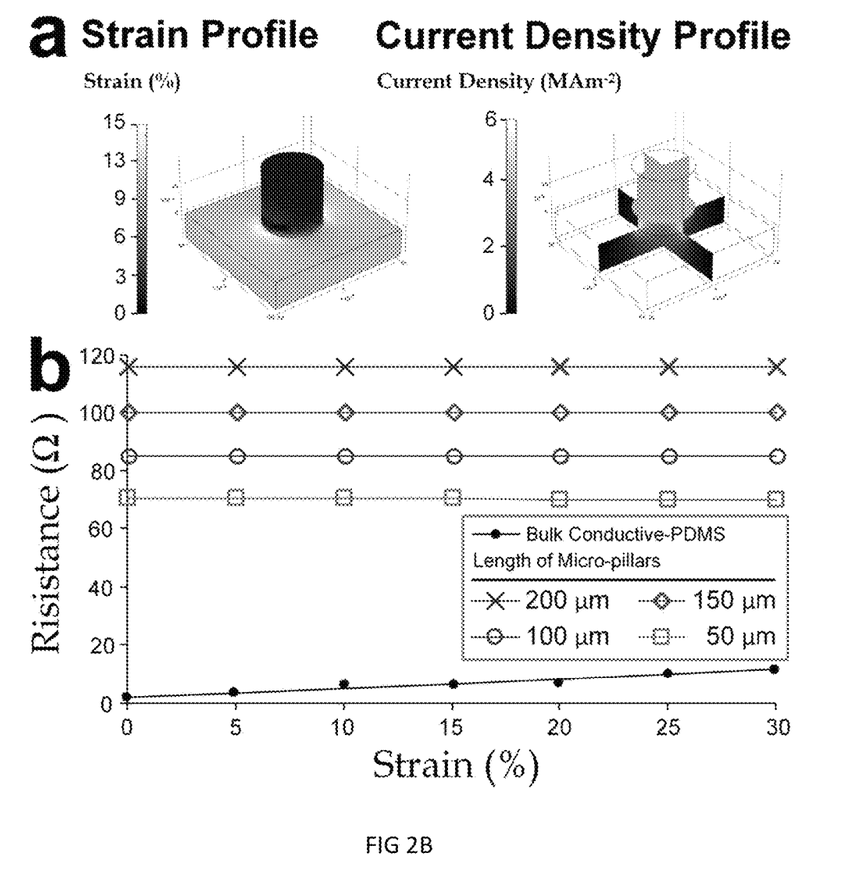
FIG. 2B includes graphical illustration showing mechanical and electrical properties of the pillar units of the electrode in FIG. 1, and a graph showing improved stability of conductivity of the pillars under stretching.

The experimental results are shown in FIG. 2a. A linear relationship can be observed for the stress versus strain, which verifies that the overall elastic moduli of the two substrates did not have noticeable changes. Some minor fluctuations between 10.1-14.5 $Sm^{-1}$ on the conductivity of the bulk conductive-PDMS can be observed. The conductivity of the micro-engineered conductive-PDMS showed a significantly higher stability (between 24.5-27.9 $Sm^{-1}$) under deformation when percentage change in considered. In addition, simulations for the bulk conductive-PDMS and micro-engineered electrodes with a range of the micro-pillar heights to obtain the strain and conductivity profiles were performed. Please see upper portion of FIG. 2B. Changes of the overall conductivity as functions of strain levels (0-30%) were examined. The simulation values (FIG. 2B) have reasonable agreements with our experiments. Results show that the bulk material is sensitive to the level of deformation, indicated by the gradient of the fitting-line. The overall conductivity of the micro-engineered electrode can be kept consistent under the range of strain increment, meaning that the micro-pillar structures can help to eliminate the deformation-induced variations in electrical properties due to body movement in practical applications. Collectively, the micro-engineered electrodes can improve the electrical performance for bio-potential detections involved in various electrophysiological applications.

Method

Figure 4:
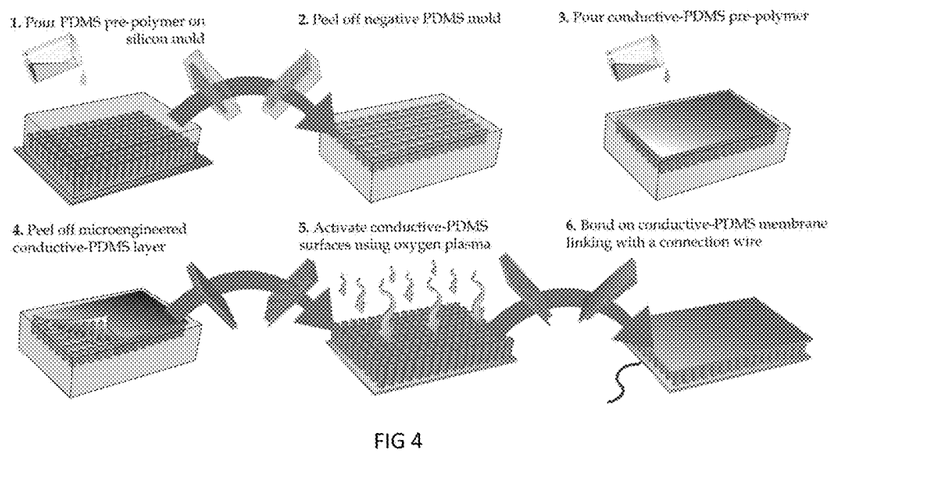
FIG. 4 are schematic diagrams showing key steps in fabrication of a conductive-PDMS electrode.

The following steps set out an embodiment of a method used to make the electrode in accordance with the present invention. Please also see FIG. 4.
1. PDMS monomer was mixed with curing agent at a ratio (% weight) of 10:1, resulting in a mixture of roughly 5-6 g. (Studies leading to the present invention have shown that the % weight may range from 5:1 to 20:1 for controlling flexibility of the electrode.)
2. Desired concentration (% weight) of dopant was added into the mixture. The concentration was calculated by the following formula:

Dopant weight (g)=PDMS mixture weight (g)/(1−mass ratio of dopant)×mass ratio of dopant.

3. The resulting mixture was stirred for 15-30 mins.
4. The mixture was poured onto a mold with microstructure pattern.
5. The mixture and mold were pressed from both sides with plastic film.
6. The sample was flattened by glass rod.
7. The sample was pressed from both sides with plexiglass.
8. Extra pressure was provided by clamps.
9. The sample was placed in the oven at 80° C. for 2 hrs. or more, depending on the rate of curing.
10. The sample was cut out of the chamber with a cutter.

In addition to the above initial steps, further steps as follows were performed for preparation of conductive PDMS ECG electrode.
1. PDMS monomer was mixed with curing agent at a ratio (% weight) of 10:1, resulting in a mixture of roughly 5-6 g.
2. The desired concentration (% weight) of dopant was added into the mixture, calculated by the following formula:

Dopant weight (g)=PDMS mixture weight (g)/(1−mass ratio of dopant)×mass ratio of dopant.

3. The resulting mixture was stirred for 15-30 mins.
4. The mixture was poured onto a piece of plastic film.
5. Pressed the mixture with another piece of plastic film.
6. The sample was flattened by glass rod.
7. The sample was pressed from both sides with plexiglass.
8. Extra pressure was provided by tongs.
9. Removed the plastic film and plexiglass.
10. Coated the PDMS layer with pattern onto this layer of conductive PDMS.
11. Moved back all the plastic film and plexiglass.
12. Extra pressure was provided by clamps.
13. The sample was placed in the oven at 80° C. for 2 hrs. or more, depending on the rate of curing.
14. The sample was cut out of the chamber with a cutter.

In the above illustration, both of parts (or layers) were fabricated with conductive PDMS. One of the electrodes is provide with multiple micropillars, while the other layer resembles a layer providing a flat surface. These two layers of electrodes were bonded together towards the end of the fabrication process. As can be seen in FIG. 3, the height of the pillars is much taller than the thickness of the base layer. This technical feature can bring technical advantage of being able to provide positive effects during signal acquisition, since the deformation of electrode would not excite the noise.

Tests performed during the course of the present invention showed working performance and physical properties were indeed desired as design. Procedures used in the tests are as follows.

Procedures for Initial Setup
1. Initial the MTS RT/30 material testing system.
2. Cover the end of the sample with some rubber for electrical insulation.
3. Place the sample between the two clamps of the testing system and clamping.
4. Place some aluminum foil onto the target area.
5. Fix the aluminum foil with small clamps.
6. Connect the sample with multi-meter through the aluminum foil.

Procedures for Measurement of Loaded Sample
1. The width and height of the target sample were measured at the midsection, the tip, and the end, using a vernier caliper.
2. The median of the measurement was recorded, and the error was recorded as the maximum deviation from the median.
3. The PDMS sample was inserted into the testing positing, and clamped tight.
4. All the parameters about the sample and the testing condition were input into the system.
5. The data about the initial state was recorded.
6. The test was started, and the sample with a certain speed was stretched.
7. According to the extension, record the corresponding data.
8. Stop the test when the extension reaches a target boundary.
9. Release the sample and export the data.

According that procedures and tests, relationships between stress, strain and conductivity are easy to be identified.

The test results show that the electrode has outstanding physical properties and stable conductivity.

As depicted above, electrodes made in accordance with the present invention can be used as dry ECG electrode. It is designed for long term ECG signal detection and monitoring. Merely contacting such electrode onto the human skin can activate the electrode. With the use of a suitable bio-signal amplifier, the ECG signal detected can be acquired and recorded. With the use of a number of such electrodes placed at different location on a subject, an ECG test can be performed. This electrode can be combined with other ECG equipment or system, such as ECG monitor and ECG jacket, in order to fulfill other specific detective application focusing on ECG or other kind of bio-signals.

It is to be noted that with the use of electrodes made in accordance with the present invention, it allows the application of the electrodes without using conductive paste. Wet electrodes or electrodes which require the use of paste causes discomfort to patients in use. Technically, it is advantageous. This novel electrode is also more durable and frequent replacement is not required. Compared to the existing wet ECG electrodes (working with gels) in the market, the present invention has a number of advantages. In addition to be able to maintain a good degree of electrical conductivity, the manufacturing of the electrodes is also more cost effective than conventional wet ECG electrodes. Operation of such electrodes is more user friendly and induce least discomfort to subject, due to for example the elimination of additional gels. The following table is a summary showing a comparison of electrodes of the present invention and the prior art at the time of filing this application.

|  | Existing ECG electrode (wet) | Our ECG electrode (dry) |
|---|---|---|
| Price (US$) | ~$0.129 | ~$0.064 |
| Frequent electrode replacement | Yes | No |
| Conductivity | Good | Good |
| Conductive medium | Yes | No |
| Comfort | No | Yes |

It should be understood that certain features of the invention, which are, for clarity, described in the content of separate embodiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. Also, a skilled person in the art will be aware of the prior art which is not explained in the above for brevity purpose.

The invention claimed is:

1. An electrographic apparatus for detection of electrical signals of a biological subject, comprising a biopotential electrode acting as a conductor, wherein:
   said electrode includes a first sheet material acting as a stretchable base layer for absorbing strain and deformation upon lateral stretching of said electrode in use;
   a plurality of conducting pillars extending from said first sheet material;
   said electrode is adapted to maintain a direct physical contact with the skin surface of a user, and the pillars are configured to remain in shape in use despite upon said lateral stretching of said electrode; and
   a radius of said pillars, a height of said pillars, and a center to center distance between two adjacent pillars are 150 um to 1 mm, 100 um to <2 mm and 500 um to 5 mm, respectively;
   whereby said electrodes are configured with said pillars to be sufficiently stiff to maintain shape thereof despite when said base layer is under strain or deformation.

2. An apparatus as claimed in claim 1, wherein said apparatus is free of gel or wet gel acting as an electrical conductive media.

3. An apparatus as claimed in claim 1, wherein said apparatus is an electrocardiographic apparatus.

4. An apparatus as claimed in claim 1, wherein said pillars have a cylindrical configuration.

5. An apparatus as claimed in claim 4, wherein said electrode is made of a polymeric material.

6. An apparatus as claimed in claim 5, wherein said electrode is made of polymeric organo-silicon compounds and conductive powders.

7. An apparatus as claimed in claim 6, wherein said organo-silicon compounds are polydimethylsiloxane (PDMS).

8. An apparatus as claimed in claim 6, wherein said conductive powders are carbon black incorporated in matrix of said polymeric organo-silicon compounds, and wherein said carbon black is acetylene black.

9. An apparatus as claimed in claim 6, wherein $$\frac{\text{weight of said carbon black}}{\text{weight of said organo} - \text{silicon compounds}}$$

ranges from $1/19$ to $1/3$.

10. An apparatus as claimed in claim 9, wherein $$\frac{\text{weight of said carbon black}}{\text{weight of said organo} - \text{silicon compounds}}$$

weight of said carbob black/weight of said organo-silicon compounds ranges from 1/5.6 to 1/4.

11. An apparatus as claimed in claim 6, wherein regions between said pillar units are made of polymeric organo-silicon compounds but not carbon black.

12. An apparatus as claimed in claim 11, wherein a gap is provided to surround said pillar units, and said gap surrounded by said regions.

13. An apparatus as claimed in claim 12, wherein said pillar units are longer than the thickness of said first or second sheet material.

14. An apparatus as claimed in claim 1, wherein the radius of said pillars, the height of said pillars, the center to center distance between said two adjacent pillars are substantially 200 um, 600 um and 1.5 mm, respectively.

15. An apparatus as claimed in claim 1, wherein said electrode includes a second sheet material, wherein said pillars are situated between said first and second sheet materials.

16. An apparatus as claimed on claim 15, wherein one of said first and second sheet materials is adapted to contact the skin of the subject, and the other sheet material is provided with a conducting wire for connection with detection circuitry of said apparatus, and wherein the sheet material adapted to contact the skin is conformable to a surface of the skin.

17. An electrode for use in an apparatus for detection of electrical signals of a biological subject, comprising a laterally stretchable base member and a plurality of pillar units extending from the first base member, said electrode made of polymeric organo-silicon compounds and carbon black, and is free of gel or wet gel acting as an electrical conductive media, wherein
   said organo-silicon compounds are polydimethylsiloxane (PDMS);
   said carbon black is in the form of powder mixed in said organo-silicon compounds; and
   a radius of said pillars, a height of said pillars, a center to center distance between said two adjacent pillars are 150 um to 1 mm, 100 um to <2 mm and 500 um to 5 mm, respectively.

18. An electrode as claimed in claim 17, wherein:

$$\frac{\text{weight of said carbon black}}{\text{weight of said organo} - \text{silicon compounds}}$$

weight of said carbon black/weight of said organo-silicon compounds is $1/19$ to $1/3$.

19. An electrode as claimed in claim 17, comprising a further base member, wherein a plurality of cylindrical pillar units is positioned between said base members.

* * * * *

UNITED STATES PATENT AND TRADEMARK OFFICE
CERTIFICATE OF CORRECTION

PATENT NO. : 10,039,466 B2  
APPLICATION NO. : 14/607110  
DATED : August 7, 2018  
INVENTOR(S) : Lam et al.

Page 1 of 3

It is certified that error appears in the above-identified patent and that said Letters Patent is hereby corrected as shown below:

In the Drawings

Replace Drawings Sheets for FIG. 1 and FIG. 3 with attached sheets

Signed and Sealed this  
Eleventh Day of December, 2018

Andrei Iancu  
*Director of the United States Patent and Trademark Office*